(12) United States Patent
Casey et al.

(10) Patent No.: US 11,027,076 B2
(45) Date of Patent: *Jun. 8, 2021

(54) NEBULIZER

(71) Applicant: Stamford Devices Limited, Galway (IE)

(72) Inventors: Michael Casey, Cornamona (IE); Joseph Grehan, Gort (IE); Kieran Hyland, Galway (IE); John Power, Moycullen (IE)

(73) Assignee: STAMFORD DEVICES LIMITED, Galway (IE)

( * ) Notice: Subject to any disclaimer, the term of this patent is extended or adjusted under 35 U.S.C. 154(b) by 415 days.

This patent is subject to a terminal disclaimer.

(21) Appl. No.: 16/019,026

(22) Filed: Jun. 26, 2018

(65) Prior Publication Data

US 2018/0361083 A1    Dec. 20, 2018

Related U.S. Application Data

(63) Continuation of application No. 13/870,376, filed on Apr. 25, 2013, now Pat. No. 10,029,053.

(Continued)

(51) Int. Cl.
| | | |
|---|---|---|
| *A61M 11/00* | (2006.01) | |
| *B05B 17/00* | (2006.01) | |
| *B05B 12/00* | (2018.01) | |

(52) U.S. Cl.
CPC ........... *A61M 11/00* (2013.01); *A61M 11/005* (2013.01); *B05B 12/00* (2013.01);
(Continued)

(58) Field of Classification Search
CPC ....... A01M 1/205; A01M 29/12; A61B 5/083; A61B 5/087; A61M 11/00; A61M 11/005;
(Continued)

(56) References Cited

U.S. PATENT DOCUMENTS

| | | | |
|---|---|---|---|
| 4,659,161 A | | 4/1987 | Holcomb |
| 5,551,416 A | * | 9/1996 | Stimpson .......... A61M 15/0085 |
| | | | 128/200.14 |

(Continued)

FOREIGN PATENT DOCUMENTS

| | | |
|---|---|---|
| CN | 2724758 Y | 9/2005 |
| CN | 201303250 | 9/2009 |

(Continued)

OTHER PUBLICATIONS

Extended European Search Report for 12166525.1—2320 dated Jul. 12, 2012 (8 pages).

(Continued)

*Primary Examiner* — Annette Dixon

(74) *Attorney, Agent, or Firm* — Bookoff McAndrews, PLLC

(57) ABSTRACT

A nebulizer comprises a controller linked at its output to a nebulizer head, and at its input to a USB cable and USB plug for connection to a host system. The link between the USB plug and the controller is a USB cable with power and data channels. The controller comprises a boost circuit, a microcontroller 11, and a drive circuit. The latter provides power and control signals via a cable and proprietary plug to the nebulizer head. These signals provide power and control for a vibrating membrane receiving a liquid to be aerosolised. The controller has a housing with LED status lamps, and an ON/OFF button. The controller can be controlled via a host, either locally or remotely.

20 Claims, 3 Drawing Sheets

Related U.S. Application Data

(60) Provisional application No. 61/642,284, filed on May 3, 2012.

(52) U.S. Cl.
CPC ... *B05B 17/0646* (2013.01); *A61M 2205/502* (2013.01); *A61M 2205/52* (2013.01); *A61M 2205/587* (2013.01); *A61M 2205/70* (2013.01)

(58) Field of Classification Search
CPC .............. A61M 11/02; A61M 11/041; A61M 15/0003; A61M 15/0085; A61M 15/02; A61M 15/025; A61M 16/0051; A61M 16/0066; A61M 16/024; A61M 16/107; A61M 16/161; A61M 16/209; A61M 2016/0021; A61M 2016/0027; A61M 2016/0036; A61M 2202/064; A61M 2205/3368; A61M 2205/3386; A61M 2205/3553; A61M 2205/3561; A61M 2205/3584; A61M 2205/3592; A61M 2205/502; A61M 2205/505; A61M 2205/52; A61M 2205/587; A61M 2205/70; A61M 2205/8206; A61M 2205/8237; A61M 2230/432; A61M 2230/435; B05B 12/00; B05B 12/081; B05B 17/0607; B05B 17/0615; B05B 17/0646; B05B 17/0669; B06B 1/0238; B06B 2201/40; B06B 2201/55; G06F 1/266

See application file for complete search history.

(56) References Cited

U.S. PATENT DOCUMENTS

| | | | |
|---|---|---|---|
| 6,615,825 | B2 | 9/2003 | Stenzler |
| 9,060,715 | B2 | 6/2015 | Schipper |
| 10,029,053 | B2 * | 7/2018 | Casey .................. A61M 11/00 |
| 2002/0038394 | A1 * | 3/2002 | Liang .................. G06F 1/266 |
| | | | 710/62 |
| 2003/0150451 | A1 | 8/2003 | Shayan |
| 2005/0011514 | A1 | 1/2005 | Power et al. |
| 2005/0284470 | A1 | 12/2005 | Wei et al. |
| 2006/0258215 | A1 | 11/2006 | Lai et al. |
| 2008/0143185 | A1 | 6/2008 | Ingles |
| 2008/0149096 | A1 | 6/2008 | Power |
| 2008/0244107 | A1 | 10/2008 | Uno |
| 2009/0058635 | A1 | 3/2009 | LaLonde et al. |
| 2009/0063187 | A1 | 3/2009 | Johnson et al. |
| 2009/0110148 | A1 | 4/2009 | Zhang et al. |
| 2009/0113093 | A1 | 4/2009 | Chen |
| 2009/0151718 | A1 * | 6/2009 | Hunter ................ A61M 15/025 |
| | | | 128/203.12 |
| 2009/0156952 | A1 * | 6/2009 | Hunter .............. A61M 16/0051 |
| | | | 600/538 |
| 2010/0056956 | A1 | 3/2010 | Dufresne et al. |
| 2010/0067197 | A1 | 3/2010 | Guccione et al. |
| 2010/0321939 | A1 | 12/2010 | Patel |
| 2011/0036346 | A1 | 2/2011 | Cohen et al. |
| 2011/0226868 | A1 * | 9/2011 | Modlin ................. A01M 1/205 |
| | | | 239/102.1 |
| 2011/0253139 | A1 | 10/2011 | Guthrie et al. |
| 2012/0003854 | A1 | 1/2012 | He |
| 2012/0099629 | A1 | 4/2012 | Faulkner et al. |
| 2012/0111970 | A1 | 5/2012 | Hogan et al. |
| 2012/0272952 | A1 | 11/2012 | Hslao |
| 2012/0303331 | A1 | 11/2012 | Niemczak et al. |
| 2013/0071808 | A1 | 3/2013 | Van der Laan |

FOREIGN PATENT DOCUMENTS

| | | |
|---|---|---|
| CN | 201781963 | 4/2011 |
| DE | 19934582 A1 | 1/2001 |
| EP | 0831384 A1 | 3/1998 |
| EP | 1184083 A1 | 3/2002 |
| EP | 2067497 A1 | 6/2009 |
| EP | 2072144 A1 | 6/2009 |
| WO | WO 2010/035252 A2 | 4/2010 |
| WO | WO 2012/026963 A2 | 3/2012 |
| WO | WO 2012/046220 A2 | 4/2012 |

OTHER PUBLICATIONS

International Search Report for PCT/EP2013/058646, dated Oct. 21, 2013 (5 pages).

* cited by examiner

NEBULIZER

CROSS REFERENCE TO RELATED APPLICATIONS

The present application is a continuation of U.S. patent application Ser. No. 13/870,376, filed Apr. 25, 2013, which claims the benefit of U.S. provisional Application No. 61/642,284, filed on May 3, 2012, the contents of all of which are herein incorporated by reference in their entireties.

INTRODUCTION

Field of the Invention

The invention relates to a nebulizer, and more particularly to power supply and control of aerosol generation in nebulizers.

Prior Art Discussion

Aerosol delivery systems can aerosolise a broad range of liquids across a particle range 1-50 μm MMAD. Such systems have an aperture plate with holes of pre-determined size and which is coupled with a vibrational mechanism powered by a piezo. The aperture plate is vibrated at a frequency of typically 120 to 150 kHz and this action causes the liquid to break surface tension and it creates an aerosol plume as droplets pass through the aperture plate. An example is described in WO2010035252 (Stamford Devices Ltd).

WO2012/026963 (Rubin) describes an aerosol delivery system having an integral USB plug.

SUMMARY OF THE INVENTION

According to the invention, there is provided a nebulizer comprising a nebulizer head for generating an aerosol, a controller for delivering power and control signals to the nebulizer head, and a standard universal bus for delivering power and control signals to the controller,
wherein the standard universal bus comprises a universal plug and a universal cable extending from said plug to the controller,
wherein the controller is linked by a cable and a plug to the nebulizer head; and
wherein the controller comprises a voltage boost circuit linked at its input with the universal bus, a processor, and a drive circuit for delivering power to the nebulizer head under control of the processor.

In one embodiment, the universal bus is a USB bus, and wherein total power requirement of the controller and of the nebulizer head falls within the power specification of the standard USB protocol.

In one embodiment, the controller provides to the nebulizer head no more than 500 mA at nominal 5V.

In one embodiment, the drive circuit is adapted to generate a waveform in the range of 120 kHz and 150 kHz.

In one embodiment, the boost circuit is adapted to generate a voltage supply for the processor and the drive circuit. Preferably, the voltage level is 12 V.

In one embodiment, the processor is adapted to upload the following information to a host via the universal bus:
power consumption, and/or
wet/dry state of the nebulizer head, and/or
nebulizer disconnect status, and/or
cable disconnect status, and/or
error or fault states, and/or
nebulization duration and time of nebulization.

In another embodiment, the controller is adapted to receive the following signals from a host via the universal bus and to use them to generate nebulizer head drive signals:
nebulization start/stop, and/or
nebulization time, and/or
nebulization flow rate, and/or
nebulization pulse rate, and/or
inspiratory/expiratory signal to enable phased nebulization In another aspect, the invention provides a nebulizer system comprising a nebulizer as defined above in any embodiment, and a host system adapted to provide control signals to the controller via said bus.

In one embodiment, the host system is adapted to provide the control signals according to a patient dosing regime.

In one embodiment, the host system includes a component adapted to communicate with a remote server for download of control instructions and/or upload of nebulizer data.

In one embodiment, the host system includes a portable device such as a smartphone or tablet computer.

DETAILED DESCRIPTION OF THE INVENTION

The invention will be more clearly understood from the following description of some embodiments thereof, given by way of example only with reference to the accompanying drawings in which:—

DESCRIPTION OF THE EMBODIMENTS

Figure 1:
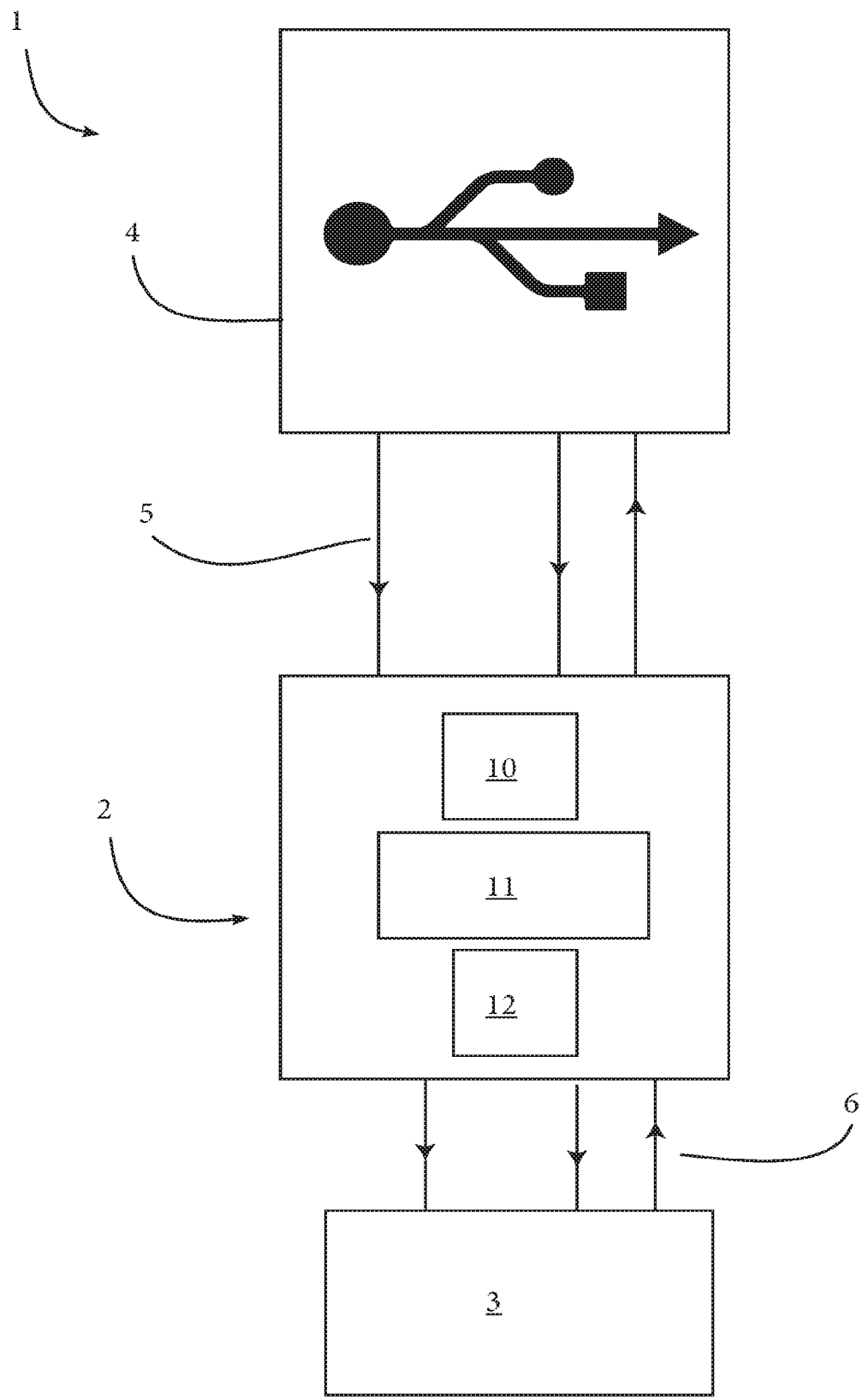
FIG. 1 is a block diagram illustrating architecture of a nebulizer of the invention.
Figure 2:
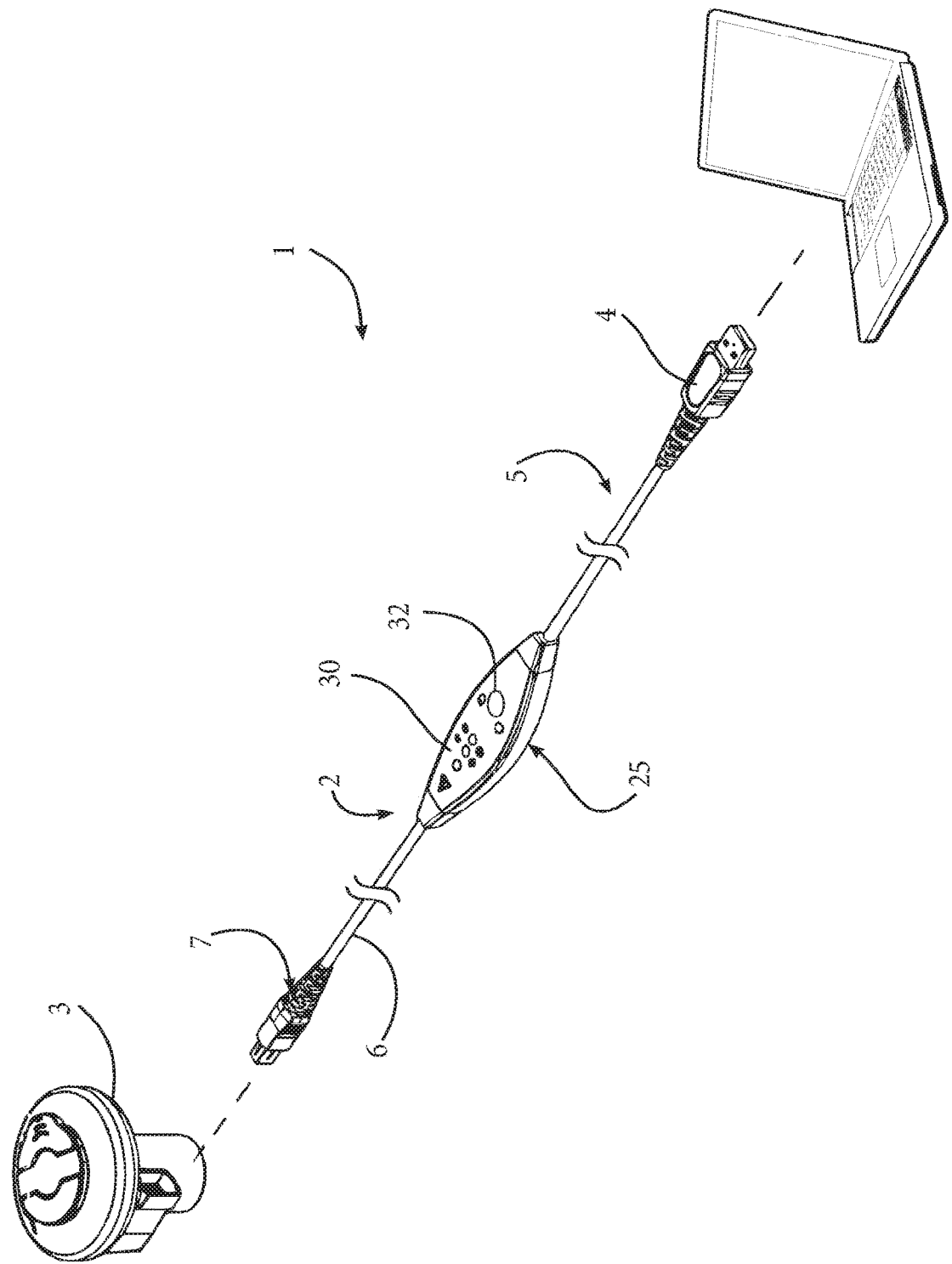
FIG. 2 is a perspective view of the nebulizer.

Referring to the drawings, a nebulizer 1 comprises a controller 2 linked to a vibrating mesh nebulizer head 3. The nebulizer 1 also comprises a USB plug 4 for connection to a host system or device.

The link between the USB plug 4 and the controller 2 is a USB (Universal Serial Bus) cable 5 with power and data channels. The link between the controller 2 and the nebulizer head 3 is a proprietary cable 6 with power and data channels and a proprietary plug 7.

The controller 2 comprises a boost circuit 10 consisting of a custom optimized high frequency, high efficiency DC to DC converter with an integrated power switch capable of providing an output voltage and current profile suitable to drive the nebulizer load, There is also a drive circuit 12 utilizing a series inductor to generate the alternating AC voltage. The drive circuit 12 incorporates a high speed MOSFET driver controlled by a pulse width modulated signal from the microcontroller. There is also a microcontroller 11 with an integrated peripheral module featuring a full speed USB 2.0 compliant interface that can automatically change clock sources and power levels upon connection to a host. The latter provides power and control signals via the proprietary cable 6 and the proprietary plug 7 to the nebulizer head 3. These signals provide power and control for a vibrating membrane receiving a liquid to be aerosolised from a feed container. An example of the nebulizer head is described in our previous PCT application WO2012/

046220. The controller 2 and the nebulizer head 3 require no more than 500 mA at nominal 5V to generate a desired aerosol.

The controller 2 has a housing 25 with LED status lamps 30, and an ON/OFF button 32. Communication takes place between the controller 2 and the USB plug 4 in compliance with the USB protocol.

The nebulizer drive circuit 12 consists of components to generate an output sine waveform of approximately 100V AC which is fed to the nebulizer head 3, causing aerosol to be generated. It uses inputs from the microcontroller 11 and the boost circuit 10 to achieve its output. The drive circuit 12 is matched to the impedance of a piezo ceramic element which causes the membrane to vibrate to ensure good energy transfer.

The microcontroller 11 generates a square waveform of 120 to 150 KHz which is sent to the drive circuit 12. The boost circuit 10 generates a nominal 12V DC voltage required by the drive circuit 12 from an input within the range of 4.75V to 5.25 V DC as per USB 2.0 electrical input requirements (released April 2000). The circuit is matched to the impedance of the piezo ceramic element within the nebulizer head 3 to ensure enhanced energy transfer. A drive frequency of 120 to 150 kHz is generated to drive the nebulizer head 3 membrane at close to its resonant frequency so that enough amplitude is generated to break off droplets and produce the aerosol. If this frequency is chopped at a lower frequency such that aerosol is generated for a short time and then stopped for a short time this gives good control of the nebulizer's flow rate. This lower frequency is called the "pulse rate".

The drive frequency may be started and stopped as required using the microcontroller 11. This allows for control of flow rate by driving the nebulizer head 3 for any required pulse rate. The microcontroller 11 may control the ON and OFF times to an accuracy of milliseconds.

The nebulizer head 3 may be calibrated at a certain pulse rate by measuring how long it takes to deliver a known quantity of solution. There is a linear relationship between the pulse rate and the nebulizer flow rate. This may allow for accurate control over the delivery rate of the aqueous solution.

Because of use of the universal bus, in this case the USB cable 5 and the USB plug 4, the controller 2 can achieve very wide-ranging control of the nebulizer head 3. Also, it allows the controller 2 to be connected to a host having data processing and USB communication capability (such as a host computer or a portable device) for upload of information previously captured from the nebulizer head 3, or for download of configuration settings or other data to the controller 2. In combination, the host and the nebulizer 1 form a system which may advantageously be used, for example, for clinical trials or controlled hospital or home treatment regimes.

The controller 2 can upload in various embodiments the following nebulizer characteristics to the host:
  power consumption, and/or
  wet/dry state, and/or
  nebulizer disconnect status, and/or
  cable disconnect status, and/or
  error or fault states, and/or
  nebulization duration and time of nebulization.

The host can in various embodiments provide the following instructions to the controller 2:
  nebulization start/stop, and/or
  nebulization time, and/or
  nebulization flow rate, and/or
  nebulization pulse rate, and/or
  inspiratory/expiratory signal to enable phased nebulization.

This will allow the controller 2 to be controlled via a host, either locally or remotely. The controller 2 may operate as a slave device, with the dosing regime determined by the host. This allows comprehensive control and treatment monitoring for a wide variety of situations such as in the home or in hospitals. If the controller is in communication with an external device, it can then act as a slave device and take commands form the external device. If it is powered by an external device, the mode of operation will be determined by the user input via the ON/OFF (power) button 32 and in this case the controller can be thought of being in "master" mode.

In other embodiments, the controller may be in the form of a hand held device, and may in fact be a mobile phone programmed to generate a user interface for nebulizer control. A specific mobile phone application could be generated to enable control of nebulization.

Figure 3:
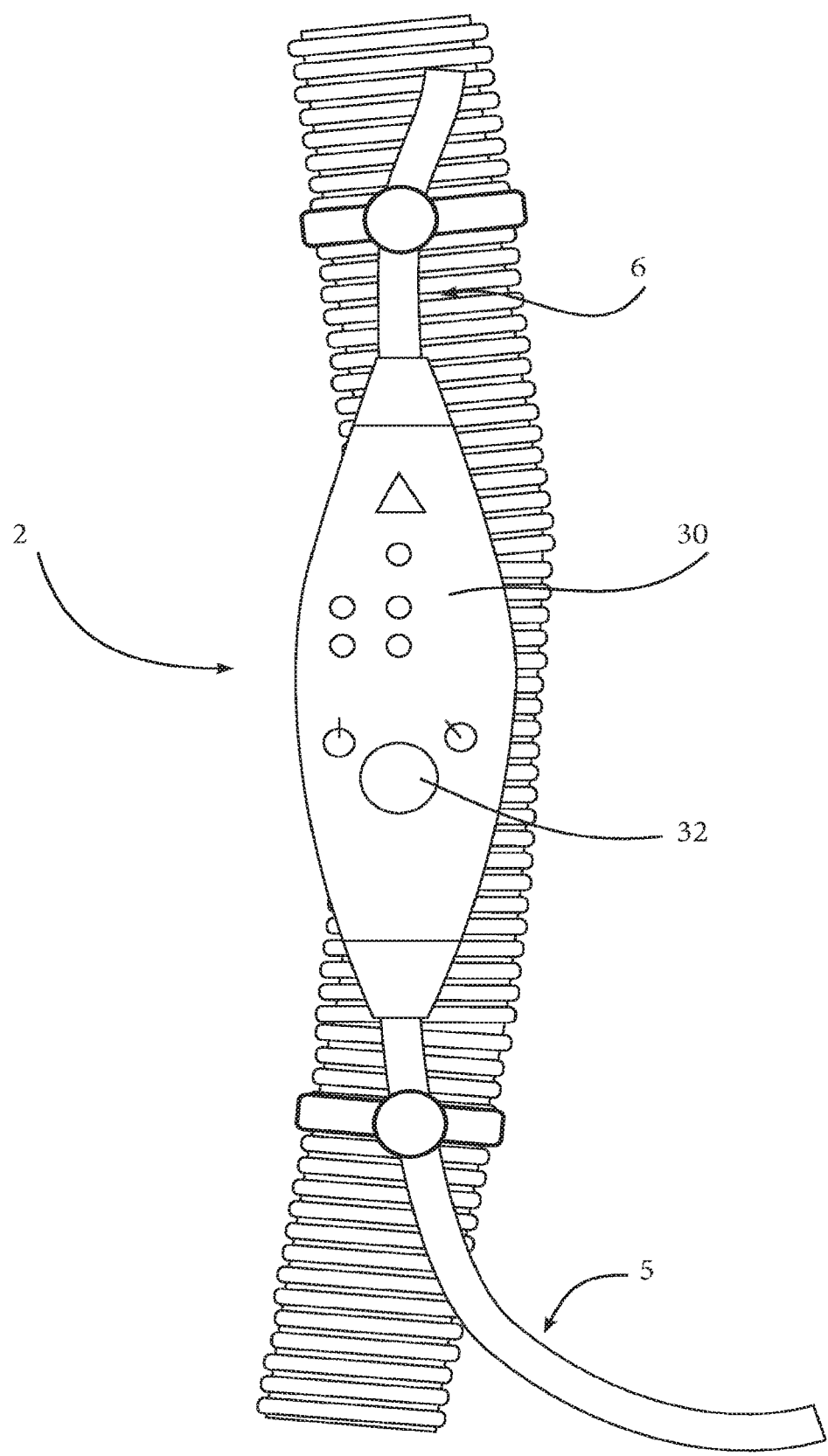
FIG. 3 shows the nebuliser in use in one example with the controller attached to a ventilation tube.

The arrangement of having the USB plug 4, the USB cable 5, the small hand-held controller 2, the proprietary cable 6 and the proprietary plug 7 allows convenience and versatility in use. For example, as illustrated in FIG. 3 the cables 5 and 6 along with the controller 2 may be secured by ties to a ventilator tube. However, they may be attached to any other tubular or elongate member. This allows convenience of access by care-givers and patients alike.

It will also be appreciated that the nebuliser can be plugged into any host system. The arrangement gives flexibility in a care-giving setting where there are multiple ventilators and patents. The USB interface allows link-up with a host device to allow remote control by a care-giver, for example, for control over the Internet to a host laptop computer into which the nebuliser is plugged.

Further, the extent of allowable local control may be limited to on/off control by limiting scope of the interface on the controller 2, the dosing control (pulse rate, flow rate, frequency etc.) being controlled from a remote location via a the host system. The controller may execute a program such as an "app" which allows a patient-specific dosing regime to be downloaded from to a mobile/tablet/PDA. The local program will then implement this new dosing regime.

There is excellent versatility because the nebuliser can be used with a ventilator, car socket, laptop computer, desktop computer, or battery pack. Because the controller is essentially part of the cabling it may not be by-passed accidentally.

The following are other benefits which arise from the invention in various embodiments:
  Increased portability due to elimination of need for additional accessories, such as battery packs, AC/DC power adapters. These are eliminated because of the common use of USB ports in general electrical equipment, such as mobile phones, computers, and medical electrical equipment
  Eliminates need for supporting brackets.
  Eliminates need for country-specific power adapters.
  Can be used in remote areas where power is not available, for example, using solar power, hand crank battery pack
  Fewer components.
  Low power consumption.
  Plug and play operation
  Can communicate with a host controller, with ability to collect patient dosing data and communicate it to the host.

Avoidance of need to integrate a control PCB into medical electrical equipment in order to operate from the ME GUI (graphical user interface). For example, it is known at present to integrate an Aerogen™ control PCB into a ventilator, to enable operation of nebulizers via the ventilator interface. The present invention will remove the need for such integration.

Compatibility/usability with wide variety of medical electrical equipment (i.e. any equipment with USB port).

Can be powered by any of a range of devices such as USB battery packs or portable solar panels.

The controller may be hand-held having a battery and power supply akin to that of a mobile phone.

The invention is not limited to the embodiments described but may be varied in construction and detail.

The invention claimed is:

1. A method for generating aerosol via a nebulizer head, comprising:
   delivering power and a plurality of control signals from a host system to a controller via a universal bus cable and a universal bus plug connectable to the host system;
   generating a plurality of nebulizer head drive signals based on the plurality of control signals via the controller; and delivering the plurality of nebulizer head drive signals to the nebulizer head via a head cable having a proprietary head plug; and
   generating aerosol via the nebulizer head according to the plurality of nebulizer head drive signals.

2. The method of claim 1, wherein the controller further includes a boost circuit, the method further including:
   generating a voltage supply for a processor and the drive circuit of the controller via the boost circuit.

3. The method of claim 2, wherein a voltage level of the voltage supply is 12V.

4. The method of claim 1, wherein the plurality of control signals includes at a nebulization flow rate signal, a nebulization pulse rate signal, or an inspiratory/expiratory signal to enable phased nebulization.

5. The method of claim 1, wherein the plurality of nebulizer head drive signals includes a wet/dry state of the nebulizer head, a nebulizer disconnect status, a cable disconnect status, an error or fault status, or a nebulization duration and time of nebulization.

6. The method of claim 1, wherein the delivering the plurality of nebulizer head drive signals to the nebulizer head is done via a drive circuit of the controller, and wherein the drive circuit generates a waveform having a frequency range between 120 kHz and 150 kHz.

7. The method of claim 1, wherein a total power requirement of the controller and of the nebulizer head falls within a power specification of USB protocol.

8. The method of claim 1, further including:
   delivering to the nebulizer head no more than 500 mA at nominal 5V from the controller.

9. The method of claim 1, wherein the head cable, controller, and bus cable form an in-line arrangement.

10. A method for generating aerosol via a nebulizer head, comprising:
    delivering power and a control signal from a host system to a controller via a universal bus cable and a universal bus plug extending from a first end of the controller, wherein the control signal includes at least one of a nebulization flow rate signal, a nebulization pulse rate signal, or an inspiratory/expiratory signal to enable phased nebulization;
    generating a nebulizer head drive signal based on the control signal via the controller;
    delivering the nebulizer head drive signal and power to the nebulizer head via a head cable having a proprietary head plug extending from a second end of the controller; and
    generating aerosol via the nebulizer head according to the nebulizer head drive signal.

11. The method of claim 10, wherein the control signal is one of a plurality of control signals, wherein each control signal of the plurality of control signals is a different type of signal than any other control signal of the plurality of control signals.

12. The method of claim 10, further including:
    uploading to the host system via the universal bus cable and universal bus plug the following nebulizer characteristic information previously captured from the nebulizer head:
    a wet/dry state of the nebulizer head,
    a nebulizer disconnect status,
    a cable disconnect status,
    an error or fault status, or
    a nebulization duration and time of nebulization.

13. The method of claim 10, wherein the generating the nebulizer head drive signal is at least partially based on a patient dosing regime.

14. The method of claim 10, further including:
    downloading control instructions from and/or uploading nebulizer data to a remote server.

15. The method of claim 10, wherein the host system includes a smartphone or tablet computer.

16. The method of claim 10, wherein the host system is one of a plurality of host systems, each host system of the plurality of host systems including varying configurations and/or functions, and wherein the controller is interchangeably coupleable to each of the plurality of host systems via the bus cable and bus plug.

17. A method for generating aerosol via a nebulizer head, comprising:
    delivering power and a plurality of control signals from a host system to a controller via a universal bus cable and a universal bus plug, wherein the plurality of control signals include two or more of a nebulization flow rate signal, a nebulization pulse rate signal, or an inspiratory/expiratory signal to enable phased nebulization;
    generating a plurality of nebulizer head drive signals based on the plurality of control signals via the controller, wherein the plurality of nebulizer head drive signals includes two or more of a wet/dry state of the nebulizer head, a nebulizer disconnect status, a cable disconnect status, an error or fault status, or a nebulization duration and time of nebulization;
    delivering the plurality of nebulizer head drive signals to the nebulizer head via a head cable having a proprietary head plug, wherein the host system, universal bus plug, universal bus cable, controller, head cable, proprietary head plug, and nebulizer head form an in-line arrangement; and
    generating aerosol via the nebulizer head according to the plurality of nebulizer head drive signals.

18. The method of claim 17, wherein the controller is interchangeably coupleable to a plurality of host systems of varying configurations and/or functions via the bus plug and bus cable.

19. The method of claim 17, further including:
    downloading control instructions from and/or uploading nebulizer data to a remote server.

20. The method of claim 17, wherein the generating the nebulizer head drive signal is at least partially based on a patient dosing regime.

\* \* \* \* \*